(12) United States Patent
Magdolen et al.

(10) Patent No.: US 7,049,344 B2
(45) Date of Patent: May 23, 2006

(54) HIGHLY SELECTIVE INHIBITORS OF THE UROKINASE PLASMINOGEN ACTIVATOR

(75) Inventors: Viktor Magdolen, Kirchheim (DE); Stefan Sperl, Muënchen (DE); Joerg Stuerzebecher, Erfurt (DE); Olaf Wilhelm, Munich (DE); Nuria Arroyo De Prada, Barcelona (ES); Luis Moroder, Martinsried (DE); Robert Huber, Germering (DE); Uwe Jacob, Munich (DE); Wolfram Bode, Gauting (DE)

(73) Assignees: Wilex Biotechnology GmbH, Munich (DE); Max-Planck-Gessellchaft zur Forderung der Wissenschaften E.V., Munich (DE)

( * ) Notice: Subject to any disclaimer, the term of this patent is extended or adjusted under 35 U.S.C. 154(b) by 0 days.

(21) Appl. No.: 10/992,844

(22) Filed: Nov. 22, 2004

(65) Prior Publication Data

US 2005/0119348 A1  Jun. 2, 2005

Related U.S. Application Data

(62) Division of application No. 10/239,074, filed as application No. PCT/EP01/02989 on Mar. 15, 2001, now Pat. No. 6,841,702.

(30) Foreign Application Priority Data

Mar. 20, 2000  (DE) ................... 100 13 715

(51) Int. Cl.
    *A61K 31/165*  (2006.01)
(52) U.S. Cl. ............ 514/619; 514/534; 514/563; 514/620
(58) Field of Classification Search .......... 514/534, 514/563, 619, 620
    See application file for complete search history.

(56) References Cited

U.S. PATENT DOCUMENTS 5,914,319 A  6/1999  Schacht et al.
6,248,738 B1  6/2001  Dickinson et al.
6,534,546 B1  3/2003  Honda et al.

FOREIGN PATENT DOCUMENTS

WO  WO 99 20608 A  4/1999
WO  WO 00 04954 A  2/2000
WO  WO 01 14324 A  3/2001

OTHER PUBLICATIONS

S. Sperl et al., "(4-Aminomethyl)phenylguanidine Derivatives As Nonpeptidic Highly Selective Inhibitors of Human Urokinase," Proceedings of the National Academy of Sciences of USA, National Academy of Science, Washington, US, vol. 97, No. 10, May 9, 2000, pp. 5113-5118, XP002169711.

R. Rai et al., "Guanidinophenyl-Substituted Enol Lactones As Selective Mechanism-Based Inhibitors of Trypsin-Like Serine Proteases," Journal of Medicinal Chemistry, American Chemical Society, Washington, US, vol. 35, No. 22, 1992, pp. 4150-4159, XP000978771.

Y, Heechung et al., "Selective Inhibition of Urokinase By Substituted Phenylguanidines: Quantitative Structure-Activity Relationship Analyses," Journal of Medicinal Chemistry, American Chemical Society, Washington, US, vol. 33, No. 11, 1990, pp. 2956-2961, XP002059264.

*Primary Examiner*—Shailendra Kumar
(74) *Attorney, Agent, or Firm*—Millen, White, Zelano, Branigan, P.C.

(57) ABSTRACT

A method is described for inhibiting urokinase plasminogen activator in a human or animal patient. The method involves administering to the patient a urokinase plasminogen activator inhibiting effective amount of a compound of the formula (I):

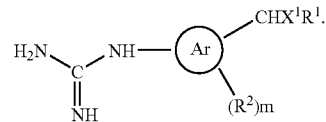

15 Claims, 2 Drawing Sheets

HIGHLY SELECTIVE INHIBITORS OF THE UROKINASE PLASMINOGEN ACTIVATOR

This application is a divisional of U.S. Ser. No. 10/239,074, filed Sep. 20, 2002; now U.S. Pat. No. 6,841,702 U.S. Ser. No. 10/239,074 is a 371 National Phase application of PCT/EP01/02989, filed Mar. 15, 2001.

DESCRIPTION

The present invention relates to novel highly selective inhibitors of the urokinase plasminogen activator (uPA, EC 3.4.21.31) of the arylguanidine type.

The urokinase-type plasminogen activator (uPA) plays a key part in tumor invasion and formation of metastases (Schmitt et al., J. Obst. Gyn. 21 (1995), 151–165) uPA is overexpressed in various types of tumor cells (Kwaan, Cancer Metastasis Rev. 11 (1992), 291–311) and binds to the tumor-associated uPA receptor (uPA-R) in which activation of plasminogen to plasmin takes place. Plasmin is capable of degrading various components of the extracellular matrix (ECM) such as fibronectin, laminin and collagen type IV. It also activates some other ECM-degrading enzymes, in particular matrix metalloproteinases. High amounts of tumor-associated uPA correlate with a higher risk of metastasizing in cancer patients (Stephens et al., Breast Cancer Res. & Treat. 52 (1998), 99–111). Therefore, inhibition of the proteolytic activity of uPA is a good starting point for an anti-metastatic therapy.

A common feature of many known synthetic uPA inhibitors is a basic residue containing amidino or guanidino groups, which can bind to $Asp^{189}$ in the uPA S1 specificity pocket and which acts as an arginine mimetic there (Spraggon et al., Structure 3 (1995), 681–691). However, most of the known inhibitors are not selective for uPA but also inhibit other serine proteases such as trypsin, thrombin, plasmin or tissue plasminogen activator (tPA).

p-Aminobenzamidine is a moderately selective uPA inhibitor having an inhibition constant of 82 μM. Billstroem et al. (Int. J. Cancer 61 (1995), 542–547) could show a distinct decrease in the growth rate of DU145 tumors (a prostate adenocarcinoma cell line) in SCID mice when administering orally a daily dose of 125 to 250 mg of p-aminobenzamidine/kg/day. The side effects were negligible.

Some monosubstituted phenylguanidines have proved effective and selective uPA inhibitors in vitro. These small molecules have inhibition constants in the micromolar range but they bind only in the S1 pocket of uPA (Yang et al., J. Med. Chem. 33 (1990), 2956–2961). Biological studies using these compounds were not carried out.

The diuretic Amiloride is a selective uPA inhibitor (Ki, uPA=7 μM) which prevents the formation of lung metastases after i.v. inoculation of rat breast adenocarcinoma cells (Kellen et al., Anticancer Res. 8 (1988), 1373–1376). Some 3-amidinophenylalanine derivatives have likewise proved effective inhibitors of serine proteases but these compounds generally have only low selectivity for uPA (Stürzebecher et al., J. Med. Chem. 40 (1997), 3091–3099; Stürzebecher et al., J. Enzyme Inhib. 9 (1995), 87–99).

Currently the most effective and most selective uPA inhibitors are benzo[b]thiophene-2-carboxamidine derivatives (B428 and B623: Ki, uPA=0.32 and 0.07 μM, respectively; U.S. Pat. No. 5,340,833). Rabbani et al. (Int. J. Cancer 63 (1995), 840–845) and also Xing et al. (Cancer Res. 57 (1997), 3585–3593) could show, after administration of 4-iodobenzo[b]thiophene-2-carboxamidine (B428), a decrease of tumor growth and metastases formation in a syngeneic model of rat prostate cancer and mouse breast cancer, respectively. The latter studies showed a further decrease in primary tumor growth when B428 was administered together with the antiestrogen tamoxifen.

The German patent application 199 40 389.9 proposes the use of arylguanidine and in particular phenylguanidine derivatives as selective uPA inhibitors. These compounds contain a further substituent on the aromatic ring system, preferably in para position to the guanidine group, which substituent contains an unsubstituted or substituted methylene group followed by hydrogen donor/acceptor functionalities. Owing to this substitution pattern; the compounds are particularly effective and selective for uPA. It is assumed that these compounds interact as arginine mimetics with the $Asp^{189}$ amino acid residue in the S1 pocket of uPA and can interact with the S2 and/or S3 pockets of uPA.

Surprisingly, further aryl guanidine derivatives have now been identified which can interact even more specifically with uPA, in particular with the amino acid residues $Gln^{192}$ and/or $Ser^{214}$. In addition to the guanidine group these compounds contain another substituent on the aromatic ring system, which contains an unsubstituted or substituted methylene group followed by a hydrogen donor function, a hydrogen acceptor function and again a hydrogen donor function.

The present invention relates to the use of compounds of the formula (I)

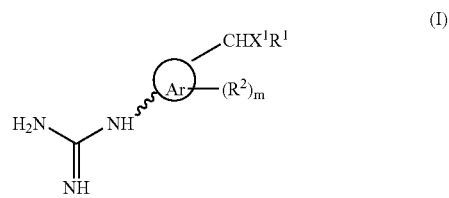

in which

Ar is an aromatic or heteroaromatic ring system, $X^1$ is a radical of the formula (IIa), (IIb) or (IIc):

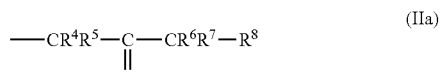

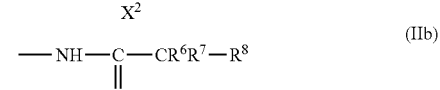

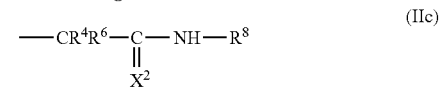

$R^1$ is H, an unsubstituted or substituted alkyl, alkenyl, alkynyl, aryl or/and heteroaryl radical, $R^2$ is halogen, $C(R^3)_3$, $C_2(R^3)_5$, $OC(R^3)_3$ or $OC_2(R^3)_5$, $R^3$ is in each case independently H or halogen, in particular F, $R^4$ and $R^5$ are H or an unsubstituted or substituted alkyl, alkenyl or alkynyl radical, where at least one of the radicals $R^4$ and $R^5$ contains a hydrogen bond donor group, for example OH, $NH_2$, SH, $OR^1$, $NHR^1$, $N(R^1)_2$, $SR^1$, CO, CS, $R^6$ and $R^7$ are H or an unsubstituted or substituted alkyl, alkenyl or alkynyl radical, where at least one of the radicals $R^6$ and $R^7$ contain a hydrogen bond donor group, for example OH, $NH_2$, SH, $OR^1$, $NHR^1$, $N(R^1)_2$, $SR^1$, CO, CS, and where $R^4$ or $R^5$ may be bridged with $R^6$ or $R^7$, $R^8$ is H or an unsubstituted or substituted alkyl, alkenyl, alkynyl, aryl or/and heteroaryl radical or $-SO_2-R^9$, where $R^6$ may or may not be bridged with $R^6$ or $R^7$, $R^9$ is H or an unsubstituted or substituted alkyl, alkenyl, alkynyl, aryl or/and heteroaryl radical, $X^2$ is a hydrogen bond acceptor group, in particular NH, $NR^{10}$, O or S, $R^{10}$ is an unsubstituted or substituted alkyl, alkenyl or alkynyl radical, and m is an integer from 0 to 4, or salts of said compounds for preparing an agent for inhibition of the urokinase plasminogen activator.

The compounds may be present as salts, preferably as physiologically tolerated acid salts, for example as salts of mineral acids, particularly preferably as hydrochlorides or as salts of suitable organic acids. The guanidinium group may carry, where appropriate, protective functions which are removable by cleavage, preferably under physiological conditions. The compounds may be present as optically pure compounds or as mixtures of enantiomers or/and diastereoisomers.

In the compounds of the formula (I), Ar is preferably an aromatic or heteroaromatic ring system having a single ring, in particular a benzene ring. In this ring system the substituents $CHX^1R^1$ and $NHC(NH)NH_2$ are preferably arranged in meta or para position and particularly preferably in para position. In addition, Ar may further contain other, non-hydrogen substituents $R^2$. The number of substituents $R^2$ is preferably 0, 1, 2 or 3, particularly preferably 0 or 1 and most preferably 0. Preferred examples of $R^2$ are halogen atoms (F, Cl, Br or I), $CH_3$, $CF_3$, OH, $OCH_3$ or $OCF_3$.

The substituent $-CHX^1R^1$ is critical for inhibitor activity. $R^1$ may be H or an unsubstituted or substituted alkyl, alkenyl, alkynyl, aryl or/and heteroaryl radical. The alkyl radical may be a straight-chain or branched $C_1-C_{10}$-alkyl group, in particular a $C_2-C_4$-alkyl group or a $C_3-C_8$-cycloalkyl group which may be substituted with, for example, $C_1-C_3$-alkoxy, hydroxyl, carboxyl, amino, sulfonyl, nitro, cyano, oxo or/and halogen or else with aryl or heteroaryl radicals. Alkenyl and alkynyl radicals are preferably $C_2-C_{10}$ groups, in particular $C_2-C_4$ groups which may be unsubstituted or substituted as described above. Aryl and heteroaryl radicals may be substituted, for example, with $C_1-C_6$-alkyl, $C_1-C_3$-alkoxy, hydroxyl, carboxyl, sulfonyl, nitro, cyano or/and oxo.

The $X^1$ group preferably contains at least one or two substituents ($R^4$ or $R^5$ or/and $R^6$ or $R^7$), which contain a hydrogen bond donor group and also a substituent $X^2$ which contains a hydrogen bond acceptor group. The hydrogen bond donor substituents contain a group which provides a hydrogen atom or/and an electron pair for a hydrogen bond. The distance of the hydrogen bond donor group from the carbon atom to which the substituents 4 and $R^5$ and, respectively, $R^6$ and $R^7$ are bound is preferably 1 to 3 carbon atoms, particularly preferably 1 to 2 carbon atoms and most preferably 1 carbon atom. Examples of hydrogen bond donor groups are OH, $NH_2$, SN, $OR^1$, $NHR^1$, $N(R^1)_2$, $SR^1$. Preferred examples of substituents containing hydrogen bond donor groups are hydroxymethyl, 2-hydroxyethyl, $-CO_2H$, $-CO_2R^1$, where $R^1$ is defined as above and is preferably an alkyl group or an aryl group such as, for example, the benzyl group, e.g. $-CO_2CH_2-Ph$, $CONH_2$, $-CONHR^1$, $CONR^1$, where $R^1$ is as defined above, e.g. $CONHCH_3$, $-CON(CH_3)_2$, CSOH, $CSOR^1$, $-COSH$, $COSR^1$, $COR^1$ and $CSR^1$, where $R^1$ is as defined above. It is also possible that two substituents containing hydrogen bond donor groups are bridged, for example via a $C_2-C_3$ bridge. Examples of substituents bridged in this way are 1,2-dihydroxyethylene or 1,3-dihydroxypropylene.

A substituent $R^4/R^5$ and, respectively, $R^6/R^7$ which contains no hydogen bond donor group is preferably hydrogen or an halogen-substituted or not halogen-substituted methyl or ethyl group. A particularly preferred substituent of this kind is hydrogen.

The hydrogen bond acceptor substituent $X^2$ is preferably NH or O, particularly preferably O.

Furthermore, the $X^1$ group contains a substituent $R^8$ which preferably carries out a steric function. $R^8$ may be hydrogen, an alkyl, alkenyl, alkynyl, aryl, heteroaryl, carboxyalkyl, carboxyalkenyl, carboxy-alkynyl, carboxyaryl or carboxyheteroaryl radical or $-SO_2-R^9$, where $R^9$ may have the same meaning as stated for $R^8$. Advantageously, $R^8$ and $R^9$ are different from hydrogen and contain at least 4, for example 6 to 20, carbon atoms. $R^8$ may or may not be bridged with $R^6$ or $R^7$.

The substituents $R^8$ and $R^9$ contain preferably space-filling groups which may be selected from the group comprising unsubstituted or substituted aryl radicals, in particular phenyl and substituted phenyl radicals and unsubstituted or substituted branched alkyl, alkenyl or alkynyl radicals, in particular with tertiary carbon atoms such as tert-butyl or neopentyl, or unsubstituted or substituted cycloalkyl radicals, in particular bi- or tricycloalkyl radicals such as adamantyl.

The compounds of the formula (I) may be prepared, for example, starting from p-aminobenzylamine according to the reaction schemes shown in the German patent application 199 40 389.9. For example, 4-aminobenzyl-amine may be reacted with a protective reagent for amino groups, for example di-tert-butyl pyrocarbonate, to give a protected intermediate, 4-(N-Boc-aminomethyl)aniline, Boc meaning tert-butyloxycarbonyl. The aromatic amino function of this compound can be reacted with a guanidinylation reagent, for example N,N'-di-Z-N"-triflylguanidine, resulting in 1-[4-(N-Boc-aminomethyl) phenyl]-2,3-di-Z-guanidine, Z being benzyloxycarbonyl. This compound can be converted to 1-[4-(aminomethyl)phenyl]-2,3-di-Z-guanidinium hydrochloride by removing the Boc protective group by cleavage. This compound may in turn be reacted with reactive compounds such as, for example, chloroformic esters, isocyanates or N-hydroxysuccinimide esters to give the desired final products.

To prepare hydrogenation-labile compounds, 4-aminobenzylamine can be reacted with a protective reagent for amino groups, for example benzyloxycarbonyl-oxysuccinimide to give a protected intermediate and then with a further guanidinylation reagent, for example N,N'-di-Boc-1-guanylpyrazole This compound can be hydrogenated and then be reacted with reactive compounds to give the desired final products.

The urokinase inhibitors of the invention may be used, where appropriate, together with suitable pharmaceutical excipients or carriers for producing medicaments or in diagnostics. In this connection, administration in combination with other active substances, for example other urokinase inhibitors such as, for example, antibodies or/and peptides, is possible.

The medicaments may be administered in humans and animals topically, orally, rectally or parenterally, for example subcutaneously or intravenously, for example in the form of tablets, coated tablets, capsules, pellets, suppositories, solutions or transdermal systems such as plasters.

The compounds of the invention are suitable for controlling disorders which are associated with pathological overexpression of uPA or/and uPAR. They are, for example, capable of very effectively inhibiting the growth or/and spreading of malignant tumors and also metastasizing of tumors. It is possible to use the uPA inhibitors, where appropriate, together with other tumor agents or with other types of treatment, for example radiation or surgery. Furthermore, the inhibitors of the invention are also effective in other uPA-associated disorders.

uPA inhibitors of the invention are preferably characterized in that they have a $K_i$ which is at least two times, preferably at least five times and particularly preferably at least 10 times and up to 1000 times lower for uPA than for tPA. It is furthermore remarkable that the compounds of the invention only marginally affect blood clotting, since their $K_i$ values are too high for effective inhibition of thrombin, plasmin and factor Xa.

The inventive substances of the formula (I) may be used in the form of conjugates with physiologically effective substances, for example radiolabels or cytotoxic agents, e.g. chemotherapeutics such as cisplatin or 5-fluoruracil, or with peptides. Furthermore, it is also possible to incorporate the substances into the membrane of carrier vesicles, for example liposomes, and thus to make possible targeting of active substances enclosed in said carrier vesicles, for example cytotoxic agents such as doxorubicin.

The present invention provides a method for inhibiting urokinase in living creatures, in particular in humans, by administering an effective quantity of at least one compound of the formula (I). The dosing of the compound is commonly in the range from 0.01 to 100 mg/kg of body weight per day. The length of treatment depends on the seriousness of the disorder and may range from a single dose up to a treatment lasting several weeks or even several months, which may be repeated at intervals, where appropriate.

Finally, the present invention relates to novel arylguanidine derivatives of the formula (I).

The invention is intended to be illustrated in more detail by the following examples and figures in which.

EXAMPLES

Materials and Methods

Figure 1:
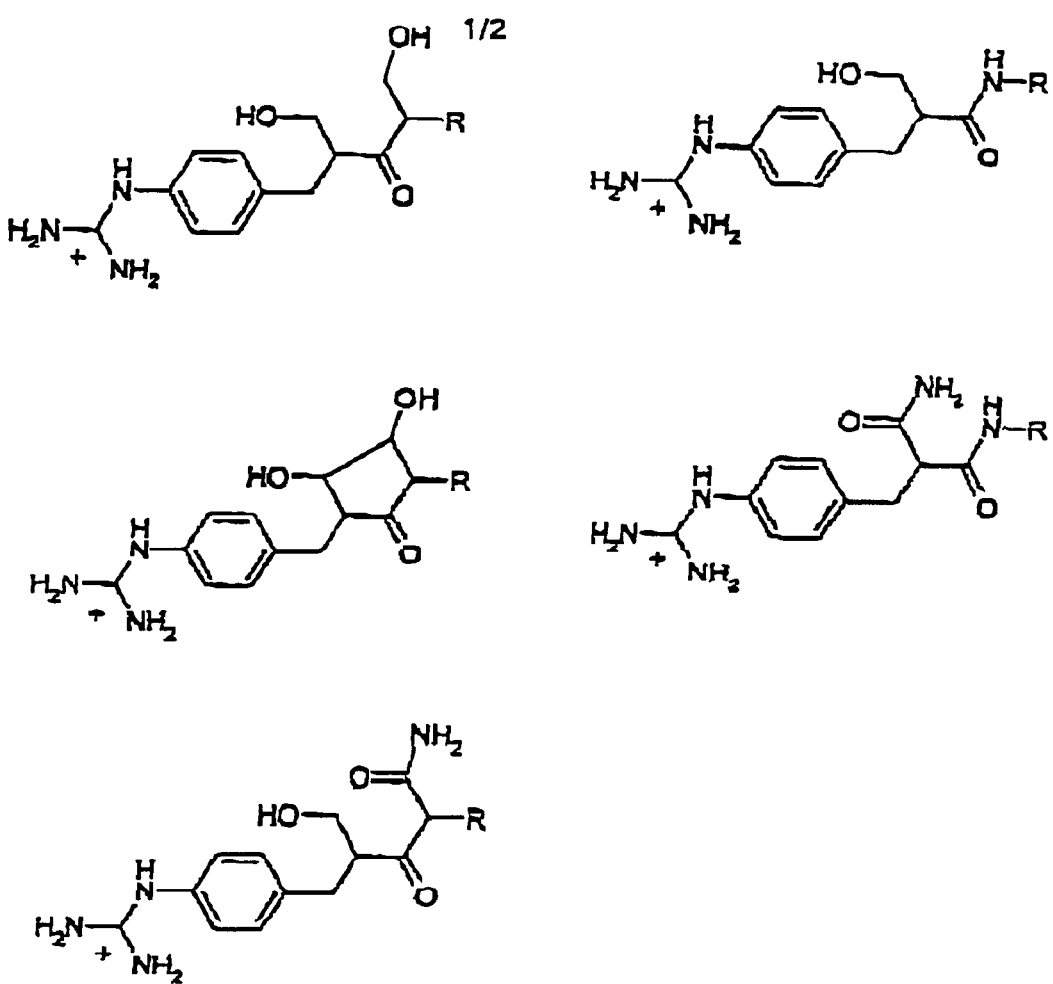
FIG. 1 shows examples for 5 compounds of the formula (I) of the invention.

All solvents and reagents used for the synthesis of uPA inhibitors were of the highest commercially available quality and were, if necessary, further purified and dried by standard methods. Analytical HPLC was carried out on Nucleosil 100/C18 columns (Macherey-Nagel, Düren, Germany) using a linear acetonitrile/2% $H_3PO_4$ gradient (from 5:95 to 90:10 in 13 min). MS spectra were measured in a Perkin Elmer API 165 mass spectrometer.

Example 1

Synthesis of Compounds of the Formula (I)

ST390: N-(4-guanidinobenzyl)-D,L-tropamide Hydrochloride 2-(1H-benzotriazol-1-yl)-1,1,3,3-tetramethyluronium tetrafluoroborate (TBTU) (23 mg; 0.07 mmol) was added to a solution of 1-[4-(aminomethyl)phenyl]-2,3-di-Z-guanidine hydrochloride (30 mg; 0.064 nmol), D,L-tropic acid (10.6 mg; 0.064 mmol), 1-hydroxybenzotriazole (HOBt) (10 mg; 0.07 mmol) and triethylamine (10 µl; 0.192 mmol) in dichloromethane (3 ml) and the solution was stirred at room temperature. After 2 h, TBTU (15 mg; 0.047 mmol) and triethylamine (10 µl; 0.192 mmol) were added once more. After another 3 h, the solution was diluted with 30 ml of dichloromethane, and washed 3× with 5% $NaHCO_3$ solution, 2× with 0.1 HCl and 1× with saturated NaCl solution. The organic phase was dried ($Na_2SO_4$) and the solvent was stripped off under reduced pressure. The Z protective groups (benzyloxycarbonyl) are removed by dissolving the compound in methanol, stirring the solution and hydrogenating the compound over a 10% palladium-activated carbon catalyst for 3 h. After removing the catalyst by filtration, the solvent was evaporated under reduced pressure. The product was recrystallized from isopropanol/diisopropyl ether after adding 1 equivalent of HCl in dioxane.

Yield: 13 mg (58%); HPLC: tk 5.6 min; MS 313 $(M+H)^+$ calculated 312 for $C_{17}H_{20}N_4O_2$ ST399: N-[4-(2,3-bis-Bocguanidino)benzyl]2-(benzyl-oxycarbonyl)-2-phenylaceataride TBTU (88 mg; 0.274 mmol) was added to a solution of 1-[4-(aminomethyl)phenyl]-2,3-di-tert-butyloxycarbonyl-guanidine hydrochloride (8) (100 mg; 0.249 mmol), monobenzyl 2-phenylmalonate (67.3 mg; 0.249 mmol), HOBt (37 mg; 0.274 mmol) and triethylamine (104 µl; 0.747 mmol) in DMF (5 ml), and the solution was stirred at room temperature overnight. After stripping off the solvent under reduced pressure, the residue was taken up in ethyl acetate (20 ml) and washed 3× with 5% $NaHCO_3$ solution, 3× with 0.5 M HCl and 1× with saturated NaCl solution. The organic phase was dried ($Na_2SO_4$) and the solvent was stripped off under reduced pressure. The product was recrystallized from ethanol/water.

Yield: 78 mg (51%); HPLC: $t_R$ 13.0 min; MS 617 $(M+H)^+$, calculated 616 for $C_{34}H_{40}N_4O_7$ ST401: N-(4-guanidinobenzyl) 2-(benzyloxycarbonyl)-2-phenylacetamide hydrochloride The Boc protective groups were removed by dissolving the compound ST399 (12 mg; 19.5 µM) in 7 M HCl/dioxane (2 ml). After 8 h the solvent was stripped off under reduced pressure and the product was recrystallized from isopropanol/diisopropyl ether.

Yield: 4 mg (454%); HPLC: $t_R$ 9.0 min; MS $(M+H)^+$, calculated 416 for $C_{24}H_{24}N_4O_3$ ST406: N-(4-guanidinobenzyl) 2-(hydroxycarbonyl)-2-phenylacetamide Hydrochloride The benzyl group was removed from compound ST399 (150 mg; 0.244 mmol) by catalytic hydrogenation in a solution of isopropanol (30 ml) and dichloromethane on a Pd/activated carbon catalyst. After 5 h the catalyst was filtered off and the solvent was stripped off. Treatment with methyl tert-butyl ether in an ultrasound bath gave the product as a light yellow powder. Subsequently, the Boc protective groups were removed, as described for ST401, and the crude product was purified by preparative HPLC.

Yield: 37 mg (42%); HPLC: $t_R$ 4.6 min; MS 327 $(M+H)^+$, calculated 326 for $C_{17}H_{18}N_4O_3$ Example 2

In-Vitro Inhibition of Urokinase by Selected Compounds of the Formula (I)

The uPA inhibitor activity was determined by incubating 200 µl of Tris buffer (0.05 mol/l, containing the inhibitor, 0.154 mol/l NaCl, 5% ethanol, pH 8.0), 25 µl of substrate (Pefachrome UK or BZ-β-Ala-Gly-Arg-pNA in $H_2O$; Pentapharm Ltd, Basle, Switzerland) and 50 μl of sc-urokinase (Ribosepharm GmbH, Haan, Germany) or another corresponding protease at 25° C. After 3 min, the reaction was interrupted by adding 25 μl of acetic acid (50%) and absorbance at 405 nm was determined by means of a microplate reader (MR 5000, Dynatech, Denkendorf, Germany). The $K_i$ values were determined by linear regression according to Dixon by means of a computer program. The $K_i$ values are the average of at least three determinations, and the standard deviation was below 25%.

Figure 2:
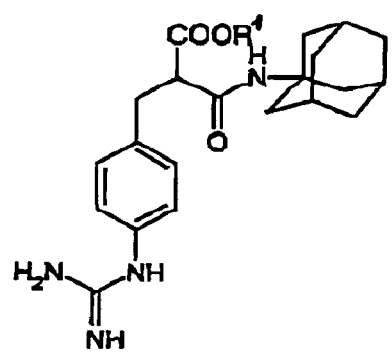
FIG. 2 shows examples for further preferred compound classes of the formula (I).
Figure 2:
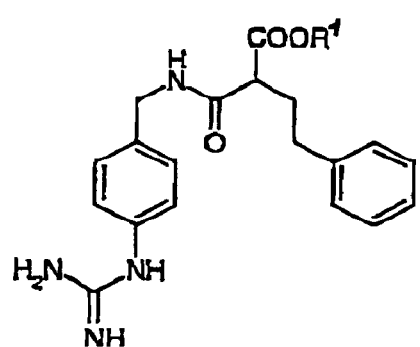
Figure 2:
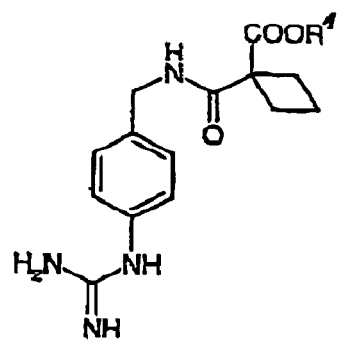
Figure 2:
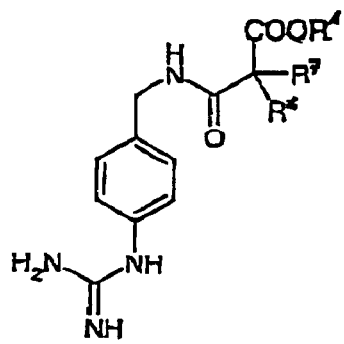

Owing to their structure, the compounds shown in FIGS. 1 and 2 can interact with the active site of uPA. The results for selected compounds of the formula (I) are listed in table 1.

TABLE 1

| No. | Formula | $K_i$ [μM] | | | | |
| --- | --- | --- | --- | --- | --- | --- |
| | | uPA | Plasmin | FXA | Thrombin | Trypsin |
| ST-390 | | 51 | >1000 | >1000 | >1000 | >1000 |
| ST-401 | | 1.4 | >1000 | >1000 | >1000 | n.t. |
| ST-406 | | <10 | n.t. | n.t | n.t | n.t |

TABLE 1-continued

| No. | Formula | $K_i$ [µM] | | | | |
|---|---|---|---|---|---|---|
| | | uPA | Plasmin | FXA | Thrombin | Trypsin |
| ST-100 | 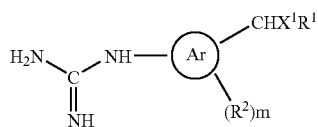 | <1 | n.t. | n.t. | n.t. | n.t. | n.t. = not tested

The invention claimed is:

1. A method of inhibiting urokinase plasminogen activator in a human or animal patient, comprising: administering to the patient a selective urokinase plasminogen activator inhibiting effective amount of a compound of the formula (I):

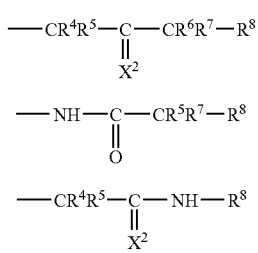

wherein,

Ar is an aromatic or heteroaromatic ring system, $X^1$ is a radical of the formula (IIa), (IIb) or (IIc):

$$—CR^4R^5—\underset{X^2}{\overset{\|}{C}}—CR^6R^7—R^8 \quad (IIa)$$

$$—NH—\underset{O}{\overset{\|}{C}}—CR^5R^7—R^8 \quad (IIb)$$

$$—CR^4R^5—\underset{X^2}{\overset{\|}{C}}—NH—R^8 \quad (IIc)$$

$R^1$ is H, an unsubstituted or substituted alkyl, alkenyl, alkynyl, aryl or heteroaryl radical, $R^2$ is halogen, $C(R^3)_3$, $C_2(R^3)_5$, $OC(R^3)_3$ or $OC_2(R^3)_5$, $R^3$ is in each case independently H or halogen, $R^4$ and $R^5$ are H or an unsubstituted or substituted alkyl, alkenyl or alkynyl radical, where at least one of the radicals $R^4$ and $R^5$ contain a hydrogen bond donor group, where the hydrogen bond donor group provides a hydrogen atom or/and an electron pair for a hydrogen bond, $R^6$ and $R^7$ are H or an unsubstituted or substituted alkyl, alkenyl or alkynyl radical, where at least one of the radicals $R^6$ and $R^7$ contains a hydrogen bond donor group, where the hydrogen bond donor group provides a hydrogen atom or/and an electron pair for a hydrogen bond and where $R^4$ or $R^5$ may be bridged with $R^6$ or $R^7$, $R^8$ is H or an unsubstituted or substituted alkyl, alkenyl, alkynyl, aryl or heteroaryl radical or $—SO_2—R^9$, where $R^8$ may or may not be bridged with $R^6$ or $R^7$, $R^9$ is H or an unsubstituted or substituted alkyl, alkenyl, alkynyl, aryl or heteroaryl radical, $X^2$ is a hydrogen bond acceptor group, which is NH, $NR^{10}$, O or S, $R^{10}$ is an unsubstituted or substituted alkyl, alkenyl or alkynyl radical, and m is an integer from 0 to 4, or a salt thereof.

2. The method of claim 1, wherein the compound is administered to the patient to treat a disorder associated with overexpression of urokinase plasminogen activator, or a receptor for it.

3. The method of claim 1, wherein the compound is administered to inhibit malignant tumor growth in a patient.

4. The method of claim 1, wherein the compound is administered to inhibit tumor metastasis in a patient.

5. The method of claim 1, wherein the compound is administered in a dose of 0.01 to 100 mg/kg of patient body weight per day.

6. The method of claim 1, wherein the compound is administered together with at least one other urokinase inhibitor.

7. The method of claim 1, wherein in the compound of formula (I), Ar is a benzene ring.

8. The method of claim 1, wherein in the compound of formula (I), the substituents —CHX$^1$R$^1$ and

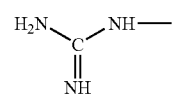

are arranged on the benzene ring in para position in relation to one another.

9. The method of claim 1, wherein in the compound of formula (I), for $R^4$, $R^5$, $R^6$ and $R^7$, the hydrogen bond donor groups are selected from OH, $OR^1$, $NH_2$, $NHR^1$, $N(R^1)_2$, SH and $SR^1$.

10. The method of claim 1, wherein in the compound of formula (I), the hydrogen bond donor group is contained in a group selected from —$CH_2OH$, —$CH_2CH_2OH$, —$CO_2H$, —$CO_2R^1$, —$CONH_2$, —$CONHR^1$, —$CON(R^{11})_2$, —COSH, —$COSR^1$, —CSOH, —$COSR^1$, —$COR^1$ and —$CSR^1$.

11. The method of claim 1, wherein in the compound of formula (I), the hydrogen bond acceptor groups for $X^2$ are selected from O and NH.

12. The method of claim 1, wherein in the compound of formula (I), $R^8$ and $R^9$ are selected from the group consisting of unsubstituted or substituted aryl radicals, unsubstituted or substituted tertiary alkyl radicals and cycloalkyl radicals.

13. The method of claim 1, wherein in the compound is administered in the form of a tablet, coated tablet, capsule, pellet, suppository, solution or transdermal system.

14. The method of claim 1, wherein in the compound of formula (I), $R^8$ and $R^9$ are selected from the group consisting of phenyl and substituted phenyl radicals, unsubstituted or substituted tertiary alkyl radicals and bicycloalkyl radicals.

15. The method of claim 1, wherein in the compound of formula (I), $R^8$ and $R^9$ are selected from the group consisting of phenyl and substituted phenyl radicals, unsubstituted or substituted tertiary alkyl radicals and an adamantyl radical.

* * * * *

UNITED STATES PATENT AND TRADEMARK OFFICE
CERTIFICATE OF CORRECTION

| | |
|---|---|
| PATENT NO. | : 7,049,344 B2 |
| APPLICATION NO. | : 10/992844 |
| DATED | : May 23, 2006 |
| INVENTOR(S) | : Nuria Arroyo-Deprada |

It is certified that error appears in the above-identified patent and that said Letters Patent is hereby corrected as shown below:

Add Claim --30. The method of claim 15, wherein the compound interacts with urokinase plasminogen activator at the $Gln^{192}$ and/or $Ser^{214}$ amino acid residues.--

Signed and Sealed this

Sixteenth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,049,344 B2  Page 1 of 1
APPLICATION NO. : 10/992844
DATED : May 23, 2006
INVENTOR(S) : Nuria Arroyo-Deprada It is certified that error appears in the above-identified patent and that said Letters Patent is hereby corrected as shown below:

Column 12, line 16, add Claim --16. The method of claim 15, wherein the compound interacts with urokinase plasminogen activator at the $Gln^{192}$ and/or $Ser^{214}$ amino acid residues.--

This certificate supersedes the Certificate of Correction issued June 16, 2009.

Signed and Sealed this

Fourteenth Day of July, 2009

JOHN DOLL
*Acting Director of the United States Patent and Trademark Office*